United States Patent [19]

Abend

[11] Patent Number: 4,885,379
[45] Date of Patent: Dec. 5, 1989

[54] NEUTRALIZED ALKYL ETHER SULFURIC ACID HALF-ESTER COMPOSITIONS CONTAINING POLYHYDROXY OLIGOMERS

[75] Inventor: Phillip G. Abend, Fort Lee, N.J.

[73] Assignee: Henkel Corporation, Ambler, Pa.

[21] Appl. No.: 180,408

[22] Filed: Apr. 12, 1988

[51] Int. Cl.$^4$ ........................................... C09C 141/08
[52] U.S. Cl. ........................................ 558/34; 558/31
[58] Field of Search ..................................... 558/34, 31

[56] References Cited

U.S. PATENT DOCUMENTS 3,393,219  7/1968  Myerly et al. ..................... 558/34

Primary Examiner—Nicky Chan
Attorney, Agent, or Firm—Ernie G. Szoke; Wayne C. Jaeschke; Real J. Grandmaison

[57] ABSTRACT

Alkyl ether sulfuric acid half-esters are neutralized in the presence of polyhydroxy oligomers such as polyglycerol to provide half-ester salt compositions of high activity and good viscosity characteristics. The products are particularly useful in shampoo formulations.

7 Claims, No Drawings

NEUTRALIZED ALKYL ETHER SULFURIC ACID HALF-ESTER COMPOSITIONS CONTAINING POLYHYDROXY OLIGOMERS

BACKGROUND OF THE INVENTION

1. Field of the Invention

Alkyl ether sulfates comprise an important class of anionic surfactants particularly extensively used in shampoos and light-duty liquid detergents. These surfactants are typically prepared by sulfation of an ethoxylated long-chain alcohol to form the corresponding sulfuric acid half-ester, followed by neutralization of the remaining acid group to a corresponding salt to improve detergency. While some sulfation methods simultaneously accomplish sulfation and neutralization of the starting ethoxylated alcohol, more usually the half-ester is first formed, as for example when sulfur trioxide, sulfuric acid, oleum, or chlorosulfuric acid are used as sulfating agents. Neutralization of the product is then customarily carried out by reaction with a suitable base to form the corresponding half-ester salt.

2. Discussion of Related Art

Although the neutralization reaction proceeds rather rapidly the solubility of alkyl ether sulfates rarely exceeds 30% activity. Accordingly, attempts to prepare more concentrated solutions by the use of hydrotropes during neutralization are now customarily effected in commercial applications by reaction of the alkyl ether sulfuric acid half-ester with an aqueous solution of an alkali metal or ammonium hydroxide in the presence of from about 15-25% by weight of a low-molecular weight alcohol, usually methanol, ethanol, or propanol. Neutralization products approaching about 60% activity can be realized by this alcoholsolubilizing procedure; however, the resulting presence of large amounts of low-molecular weight alcohol in the finished product is generally undesirable owing to the resultant flammability of the solutions and decrease in viscosity of the product which adversely affects the viscosity requirement of shampoos and other viscosity-dependent detergent compositions prepared from the alcohol-contaminated products.

It is accordingly desirable to provide a process for the production of neutral alkyl ether sulfate compositions useful in shampoo and other detergent-based compositions which are free of low molecular weight alcohols and which retain a high activity.

DESCRIPTION OF THE INVENTION

Other than in the operating examples, or where otherwise indicated, all numbers expressing quantities of ingredients or reaction conditions used herein are to be understood as modified in all instances by the term "about".

According to the invention, alkyl ether sulfate compositions are prepared by neutralization of an alkyl ether sulfuric acid half-ester of the formula

$$RO(CH_2CH_2O)_nSO_3H$$

wherein R is $C_{10}-C_{20}$-alkyl and n is from 1 to 7, with a neutralizing agent in the presence of a polyhydroxy oligomer compound such as a polyglycerol or a hydrogenated, hydrolyzed polysaccharide, for example hydrolyzed corn syrup solids.

Neutralization of the sulfuric acid half ester is carried out with a neutralizing agent of the type used in prior art neutralizing processes, particularly an agent which provides an alkali metal, alkaline earth metal, alkanolamine, or ammonium salt of the sulfuric acid half-ester. Particularly suitable neutralizing agents include potassium, sodium, or ammonium hydroxides and mono-, di-, or triethanolamine. The neutralization process is carried out in the presence of sufficient polyhydroxy oligomer to provide a product having an activity of at least about 45% as measured by titration with a standard cationic surfactant. If the neutralized, alcohol-free salt is to be used in a shampoo or other viscosity dependent formulation, the use of large amounts of polyhydroxy oligomer which might adversely affect the desired viscosity characteristics of the shampoo is not recommended. Generally, amounts of polyhydroxy oligomer of from about 2% to 15% by weight, based on the weight of the alkyl ether sulfuric acid half-ester are employed; and preferably, amounts in the range of from about 5% to 10% by weight are employed, primarily for economic reasons. This latter narrow range is particularly suitable when the neutral sulfate is to be used in shampoos, as such amounts of polyhydroxyoligomer tend not to decrease the viscosity of typical prior art shampoo formulations.

Suitable polyglycerols are those oligoglycerols of the type produced by dehydration of glycerol with condensation of the dehydrated monomers. Generally, polyglycerols of the type described in "Structures in 'Polyglycerol'", Dolhaine, et al., *Henkel-Referate* 21, Int. Ed. Henkel KGaA, Dusseldorf (pub.)

(1985), are useful, particularly oligoglyceroles having 2-10 glycerol groups and preferably products predominately comprising tetramers, pentamers, hexamers, or heptamers of glycerol. A commercially available polyglycerol useful in the practice of the invention is Polyglycerol 06, a product of Mazer Chemical Co. The hydrogenated, hydrolyzed corn syrup solids useful in the practice of the invention are of the type described as hydrogenated starch hydrolysates in CTGA Dictinary, 3rd Edition Supplement, 1985, p. 36. Other polyhydroxy oligomers the invention include cyclodextrins and alkyl polyglycosides.

Typically, an alkyl ether sulfuric acid half ester of the above-described formula is neutralized according to the process of the invention by addition of the half-ester to an aqueous solution of the neutralizing agent and polyhydroxy oligomer. Advantageously, sodium chloride is added to necessary to increase the viscosity of the composition as desired, as is known in the prior art. The pH is adjusted to neutral or slightly alkaline as required, suitably with 25% NaOH or 50% citric acid, or a combination thereof. On mixing, a neutralized alkyl ether half-ester composition according to the invention, typically having an activity in excess of 50%, is obtained.

The alkyl ether sulfuric acid half-ester neutralized according to the invention is conveniently used in shampoo formulations comprising the half-ester neutralization product as the sole or primary detergency ingredient. Useful shampoos include compositions comprising the neutralization product diluted with water to the desired viscosity. Shampoo compositions according to the invention optionally include standard ingredients such as thickeners, perfumes, foaming agents, conditioning agents, compatible auxiliary surfactants, dyes, pearlescing agents, and opacifiers.

The following Examples illustrate the practice of the invention.

EXAMPLE I

A. Preparation of highly active half-ester salt using post addition

Charge:

| | |
|---|---|
| Alkyl ether sulfate half-ester[1] (3.04 meq/g H+) | 400 g. |
| 50% NaOH | 9 g. |
| NaCl | 12 g. |
| Polyglycerol[3] (50% aqueous solution) | 80 g. |
| H$_2$O | 210 g. |

Procedure:

The half-ester (chilled) was added in a slow stream to a cooling mixture of the other components, and the pH adjusted with 25% NaOH/50% citric acid to 7.5.

The product had an activity of 55.16% and a viscosity of 7,000 cps.

B. Preparation of detergent composition using neutralized product from IA

To 202 g of active material, 21 g of H$_2$O was added. The viscosity of the product was 10,500 cps.

EXAMPLE 2

Preparation of highly active half-ester salt using polyglycerol

Charge:

| | |
|---|---|
| Alkyl ether sulfate half-ester[2] (3.16 meq/g H+) | 400 g. |
| 50% NaOH | 103 g. |
| NaCl | 12 g. |
| Polyglycerol[3] (50% aqueous solution) | 80 g. |
| H$_2$O | 205 g. |

Procedure:

The procedure of Example IA was followed. The pH was adjusted with 25% NaOH/50 citric acid to 7.9.
Activity: 51/13%
Viscosity: 7500 cps.

EXAMPLE 3

A. Preparation of highly active half-ester salt using polyglycerol

Charge:

| | |
|---|---|
| Alkyl ether sulfate half-ester[2] (3.19 meq/g H+) | 370. g. |
| NaCl | 11.1 g. |
| Polyglycerol[3] (50% aqueous solution) | 74. g. |
| NH$_4$OH (28% aqueous) | 117 ml. |
| H$_2$O | 180 g. |

Procedure:

The half-ester was added slowly to a cooled solution of NaCl and aqueous polyglycerol; 82 ml. NH$_4$OH in H$_2$O was then added. When the pH fell below 6, 10 ml. of NH$_4$OH was added. 2 additional 10 ml. portions, followed by a 5 ml. portion, of NH$_4$OH were further added. The reaction mixture was then mixed for 15 mins. A very thick product was obtained, having the following characteristics:

| | |
|---|---|
| pH | 7.39 |
| Viscosity | 6500 cps |
| Activity | 52.06% |
| Unsulfated Alcohol | 1.42% |

-continued

| | |
|---|---|
| NH$_4$Cl | 1.72% |
| (NH$_4$)$_2$SO$_4$ | 0.71% |

B. Preparation of detergent composition

To 300 g. of 52.06% active material was added 8 g. H$_2$O. The mixture was mixed well, and spun down. The composition had a viscosity of 4950 cps.

EXAMPLE 4

Preparation of half-ester salt using HYSTAR 5875.

Charge:

| | |
|---|---|
| Alkyl ether sulfate half-ester[2] (3.16 meq/g H+) | 400 g. |
| HYSTAR 5875[4] | 53 g. |
| NaCl | 12 g. |
| H$_2$O | 220 g. |
| NH$_4$OH (28% aqueous) | 135 g. |

Procedure:

The procedure of Example 3A was followed, using 80 g. NH$_3$ and HYSTAR 5875 instead of polyglycerol. After about 1/3 of the halfester was added, the thick paste naturally formed began to thin out. 55 g. of the NJ$_4$OH was then further added to maintain the pH at 7. The product has the following characteristics:
Activity: 47.16%
Viscosity: 11,500 cps.

EXAMPLE 5

A. Preparation of half-ester salt using HYSTAR 6075

Charge:

| | |
|---|---|
| Alkyl ether sulfate half-ester[2] (3.16 meq/g H+) | 400 g. |
| HYSTAR 6075[5] | 54.5 g. |
| NaCl | 12 g. |
| H$_2$O | 200 g. |
| NH$_4$OH (28% aqueous solution) | 137 ml. |

Procedure:

The procedure of Example 3A was followed, using 87 ml NH$_3$ followed by 50 ml to maintain alkalinity. The solution was spun down several times and the pH was adjusted with 50% citric acid/aq NH$_3$ to about 7.2.
Activity: 53.23%
Viscosity: 17,000 cps.

B. Preparation of detergent composition

To 462 g. of 53.23% active material from 5A, 18.3 g. of H$_2$O was added. The product was mixed well and spun down. The composition had the following characteristics:

| | |
|---|---|
| Viscosity | 11,500 cps. |
| Activity | 50.69% |
| US | 1.34% |
| NH$_4$Cl | 1.42% |
| (NH$_4$)$_2$SO$_4$ | 0.85% |

EXAMPLE 6

A. Preparation of half-ester salt using HYSTAR 6075

| | |
|---|---|
| Frozen (then thawed at room temperature) alkyl | 400 g. |

| | |
|---|---|
| ether sulfate half-ester[1] acidity 3.0 meq/g H+) | |
| 50% NaOH | 99 g. |
| HYSTAR 6075[5] | 53 g. |
| NaCl | 12 g. |
| H$_2$O | 225 g. |

The procedure of Example IA was followed, and the product adjusted to pH 7.37 and spun down. The following characteristics were observed:
Viscosity: 9,500 cps.
Activity: 55.82%

B. Preparation of detergent composition

To 500 g. of 55.82% active material from 6A, 19 g. of H$_2$O was added. The mixture was mixed well and spun down. The composition had a viscosity of 25,700 cps.

EXAMPLE 7

Preparation of half-ester salt using polyglycerol.

Charge:

| | |
|---|---|
| Alkyl ether sulfate half-ester[2] | 400 g. |
| Polyglycerol[6] (50% aqueous solution) | 80 g. |
| NaCl | 12 g. |
| H$_2$O | 180 g. |
| NH$_4$OH (28% aqueous solution) | 110 ml. |

Procedure:
The procedure of Example 3A was followed, initially using 100 ml NH$_4$OH, and the pH adjusted to 7.0 with a further 10 ml. portion NH$_4$OH. The product has the following characteristics:
Activity: 52.6%.
Viscosity: 2750 cps

EXAMPLE 8

Preparation of Highly Active Half-Ester Salt Using Polyglycol

Charge:

| | |
|---|---|
| Alkyl ether sulfate half-ester[2] (3.16 meq/gH+) | 406 g. |
| NH$_4$OH | 130 ml. |
| NaCl | 12 g. |
| Polyglycerol[3] (50% aqueous solution) | 48 g. |
| Polyethylene Glycol 400 | 8 g. |
| H$_2$O | 220 g. |

Procedure:
The procedure of Example 3 was followed. The pH of the mixture was adjusted with 50% citric acid and NH$_4$OH to 6.8 (as is). The product had the following characteristics:

| | |
|---|---|
| pH (as is) | 6.8 |
| Activity | 49.4% |
| Viscosity | 3,680 cps |

EXAMPLE 9 (Comparative Example)

Evaluation of high active alkylether sulfate

The highly active alkyl ether sulfate half-ester obtained in Example 2 was evaluated against a commercial half-ester salt preparation. The results indicate that foam characteristics and viscosity potentiation are comparable.

| | A | B |
|---|---|---|
| Commercial product[7] | 45.90 | — |
| Standamid TM LDS[8] | 3.00 | 3.00 |
| Example 3 product | — | 23.52 |
| Water | 51.10 | 73.48 |
| 0.50% NH$_4$Cl | 1,250 cps | 3,400 cps |
| 1.00% NH$_4$Cl | 12,000 cps | 15,000 cps |
| 1.50% NH$_4$Cl | 20,000 cps | 20,000 cps |
| 2.00% NH$_4$Cl | 17,600 cps | 27,200 cps |
| 2.50% NH$_4$Cl | 10,000 cps | 9,000 cps |
| Foam (ml.) | 285 | 285 |

METHODS AND MATERIALS (EXS 1-9)

1. Methods

All viscosities are Brookfield measurements at room temperature (spindle #4, 6rpm) unless otherwise indicated. Foam characteristics were evaluated by High Speed Agitation (Blender) Foam Generation Test.

2. Materials

Alkyl ether sulfate half-ester[1]: Standapol ESP Sauer ester sodium lauryl (C$_{12}$–C$_{14}$) 2 EO sulfate.
Alkyl ether sulfate half-ester[2]: Standapol ES-1 Sauer ester sodium lauryl (C$_{12}$–C$_{14}$l) EO sulfate.
Polyglycerol[3]: Polyglycerol 06 6 mole oligomer of glycerol.
HYSTAR TM 5875[4] Carbohydrate: hydrogenated starch hydrolyzate.
HYSTAR TM 6075[5] Carbohydrate: hydrogenated starch hydrolyzate.
Polyglycerol[6]: Polyglycerol HOB257-26 6 mole oligomer of glycerol.
Commercial product[7]: Standapol EA-1, Ammonium lauryl (C$_{12}$–C$_{14}$) 1 EO sulfate.
Standamid TM LDS[8]: lauric (C$_{12-18}$) diethanolamide.

I claim:
1. A process for the neutralization of an alkyl ether sulfuric acid half-ester of the formula

$$RO(CH_2CH_2O)_nSO_3H$$

wherein R is C$_{10}$–C$_{20}$ alkyl and n is from 1 to 7, comprising neutralizing the half-ester with a neutralizing agent in aqueous solution in the presence of a polyhydroxy oligomer selected from the group consisting of a polyglycerol or a hydrogenated, hydrolyzed polysaccharide to provide the corresponding half-ester salt.

2. The process of claim 1 wherein the neutralizing agent converts the half-ester to the corresponding alkali metal, alkaline earth metal, ammonium, r alkanolamine salt.

3. The process of claim 1, wherein the polyhydroxy oligomer is an oligoglycerol having 2–10 glycerol groups.

4. The process of claim 1, wherein the polyhydroxy oligomer is a polyglycerol selected from the group consisting of tetramers, pentamers, hexamers and heptamers of glycerol.

5. The process of claim 2, wherein the neutralizing agent is sodium, potassium or ammonium hydroxide, mono-, di-, or triethanolamines.

6. The process of claim 1, wherein the polyhydroxy oligomer is employed in an amount of from about 2 to 15% by weight of the alkyl ether halfester.

7. The process of claim 4, wherein the polyhydroxy oligomer is employed in an amount of from about 5 to 10% by weight of the half-ester.

* * * * *